United States Patent
Furuhashi et al.

(10) Patent No.: US 10,573,504 B2
(45) Date of Patent: Feb. 25, 2020

(54) ORTHOGONAL ACCELERATION TIME-OF-FLIGHT MASS SPECTROMETRY

(71) Applicant: SHIMADZU CORPORATION, Kyoto-shi, Kyoto (JP)

(72) Inventors: Osamu Furuhashi, Kyoto (JP); Daisuke Okumura, Kyoto (JP); Tomoyuki Oshiro, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 16/070,088

(22) PCT Filed: Jan. 15, 2016

(86) PCT No.: PCT/JP2016/051089
§ 371 (c)(1),
(2) Date: Jul. 13, 2018

(87) PCT Pub. No.: WO2017/122339
PCT Pub. Date: Jul. 20, 2017

(65) Prior Publication Data
US 2019/0019664 A1    Jan. 17, 2019

(51) Int. Cl.
*H01J 49/40* (2006.01)
*H01J 49/06* (2006.01)
(Continued)

(52) U.S. Cl.
CPC ............ *H01J 49/401* (2013.01); *G01N 27/62* (2013.01); *H01J 49/063* (2013.01); *H01J 49/067* (2013.01);
(Continued)

(58) Field of Classification Search
CPC ...... H01J 49/401; H01J 49/063; H01J 49/067; H01J 49/105; H01J 49/24; H01J 49/403; G01N 27/62
(Continued)

(56) References Cited

U.S. PATENT DOCUMENTS 5,689,111 A    11/1997 Dresch et al.
6,285,027 B1    9/2001 Chernushevich et al.
(Continued)

FOREIGN PATENT DOCUMENTS

CA    2 255 122 A1    6/2000
CA    2 349 416 A1    11/2002
(Continued)

OTHER PUBLICATIONS

M. Guilhaus et al., "Orthogonal Acceleration Time-of-Flight Mass Spectrometry," Mass Spectrometry Reviews, 2000, pp. 65-107, vol. 19.
(Continued)

*Primary Examiner* — Nicole M Ippolito
(74) *Attorney, Agent, or Firm* — Sughrue Mion, PLLC

(57) ABSTRACT

A multipole ion guide (30) including a plurality of rod electrodes arranged at an angle to the central axis (C) is placed within a collision cell (13) located in the previous stage of an orthogonal accelerator (16). Radio-frequency voltages with opposite phases are applied to the rod electrodes of the ion guide (30) so that any two rod electrodes neighboring each other in the circumferential direction have opposite phases of the voltage. A depth gradient of the pseudopotential is thereby formed from the entrance end toward the exit end within the space surrounded by the rod electrodes, and ions are accelerated by this gradient. During an ion-accumulating process, a direct voltage having the same polarity as the ions is applied to the exit lens electrode
(Continued)

(132) to form a potential barrier for accumulating ions. Among the ions repelled by the potential barrier, ions having smaller m/z return closer to the entrance end. Therefore, when the potential barrier is removed and ions are discharged, ions having smaller m/z are discharged at later points in time than those having larger m/z. Therefore, a wide m/z range of ions can be simultaneously accelerated and ejected by an orthogonal accelerator (16).

8 Claims, 7 Drawing Sheets

(51) Int. Cl.
  *H01J 49/10* (2006.01)
  *H01J 49/24* (2006.01)
  *G01N 27/62* (2006.01)
(52) U.S. Cl.
  CPC ............ *H01J 49/105* (2013.01); *H01J 49/24* (2013.01); *H01J 49/403* (2013.01)
(58) Field of Classification Search
  USPC .................... 250/281, 282, 283, 286, 287
  See application file for complete search history.

(56) References Cited

U.S. PATENT DOCUMENTS

| | | | |
|---|---|---|---|
| 6,770,872 B2 | 8/2004 | Bateman et al. | |
| 7,087,897 B2 | 8/2006 | Bateman et al. | |
| 7,208,726 B2 | 4/2007 | Hidalgo et al. | |
| 7,456,388 B2 | 11/2008 | Loboda et al. | |
| 7,714,279 B2 | 5/2010 | Franzen | |
| 2002/0030159 A1 | 3/2002 | Chernushevich et al. | |
| 2005/0247872 A1 | 11/2005 | Loboda et al. | |
| 2005/0279931 A1* | 12/2005 | Franzen | H01J 49/0077 250/290 |
| 2007/0158545 A1* | 7/2007 | Verentchikov | H01J 49/004 250/282 |
| 2011/0284741 A1* | 11/2011 | Stoermer | H01J 49/0072 250/292 |
| 2015/0364309 A1* | 12/2015 | Welkie | H01J 49/062 250/282 |
| 2016/0155624 A1* | 6/2016 | Verenchikov | H01J 49/004 250/283 |

FOREIGN PATENT DOCUMENTS

| | | |
|---|---|---|
| CA | 2 565 455 A1 | 11/2005 |
| EP | 1 006 559 A2 | 6/2000 |
| EP | 1 743 354 A | 1/2007 |
| EP | 1743357 | 1/2007 |
| JP | 2007-536714 A | 12/2007 |
| JP | 2011-175982 A | 9/2011 |
| JP | 4872088 B2 | 2/2012 |
| WO | 2005/106921 A1 | 11/2005 |
| WO | 2005/106922 A1 | 11/2005 |

OTHER PUBLICATIONS

International Search Report for PCT/JP2016/051089 dated Apr. 12, 2016 (PCT/ISA/210).
Extended European Search Report dated Nov. 30, 2018 issued by the European Patent Office in counterpart application No. 16884942.0.

* cited by examiner

ORTHOGONAL ACCELERATION TIME-OF-FLIGHT MASS SPECTROMETRY

CROSS REFERENCE TO RELATED APPLICATIONS

This application is a National Stage of International Application No. PCT/JP2016/051089 filed Jan. 15, 2016.

TECHNICAL FIELD

The present invention relates to an orthogonal acceleration time-of-flight mass spectrometer, and more specifically, to an ion-introducing section for introducing ions into an orthogonal accelerator which ejects ions in an orthogonal acceleration time-of-flight mass spectrometer.

BACKGROUND ART

In normal types of time-of-flight mass spectrometers, a specific amount of kinetic energy is imparted to ions derived from a sample component to make those ions fly a specific distance in a spatial area. The period of time required for their flight is measured, and the mass-to-charge ratio of each ion is calculated from its time of flight. Therefore, if there is a variation in the position of the ions or in the amount of initial energy of the ions at the time when the ions are accelerated and begin to fly, a variation in the time of flight of the ions having the same mass-to-charge ratio occurs, which leads to a deterioration in the mass-resolving power or mass accuracy. As a technique for solving such a problem, an orthogonal acceleration time-of-flight mass spectrometer, which accelerates ions into the flight space in a direction orthogonal to the incident direction of the ion beam, has been commonly known (this device is hereinafter appropriately abbreviated as the "OA-TOFMS").

As just described, the OA-TOFMS is configured to accelerate ions in a pulsed fashion in the direction orthogonal to the direction in which a beam of ions derived from a sample component is initially introduced. Such a configuration allows the device to be combined with various types of ion sources which ionize components contained in a continuously introduced sample, such as an atmospheric pressure ion source (e.g. electrospray ion source) or electron ionization source. In recent years, the so-called "Q-TOF mass spectrometer" has also been widely used for structural analyses of compounds or similar purposes. In this device, the OA-TOFMS is combined with a quadrupole mass filter for selecting an ion having a specific mass-to-charge ratio from ions derived from a sample component as well as a collision cell for dissociating the selected ion by collision-induced dissociation (CID).

In the Q-TOF mass spectrometer, since CID gas is continuously or intermittently introduced into the collision cell, the gas pressure within the collision cell becomes comparatively high. Therefore, when ions having various mass-to-charge ratios exit from the collision cell, all ions have already been sufficiently cooled and have approximately equal amounts of kinetic energy. Accordingly, an ion with a smaller mass-to-charge ratio has a higher speed when arriving at the orthogonal accelerator in the OA-TOFMS. This causes a problem related to the duty cycle in the Q-TOF mass spectrometer, as will be hereinafter described (see Non Patent Literature 1).

FIG. 12 is a schematic diagram of an ion optical system including the sections from the collision cell to the orthogonal accelerator in a conventional Q-TOF mass spectrometer. Consider the case where various ions which have been sufficiently cooled within the collision cell 13 as described earlier are introduced through an ion transport optical system 14 (which is an electrostatic lens electrode) into the orthogonal accelerator 16 along the X-axis direction. The orthogonal accelerator 16 includes a plate-shaped push-out electrode 161 and grid-shaped extraction electrodes 162. A pulsed acceleration voltage is applied to those electrodes at constant frequency f, whereby the ions introduced into the orthogonal accelerator 16 are ejected toward the flight space (not shown) in the Z-axis direction. The ions to be ejected from the orthogonal accelerator 16 by this operation are ions which are present within a range having length L along the incident direction of the ions into the orthogonal accelerator 16 (X-axis direction). This range corresponds to the opening of the extraction electrodes 162. Ions introduced into the orthogonal accelerator 16 within the period of time (1/f) from one ejection of the ions to the next ejection of the ions directly pass through the orthogonal accelerator 16 and are eventually wasted.

Letting v denote the speed of an ion entering the orthogonal accelerator 16, the use efficiency of the ion, i.e. duty cycle ε, is defined as follows:

$$\varepsilon = fL/v$$

As noted earlier, the speed v of an ion depends on the mass-to-charge ratio of the ion. Therefore, the smaller the mass-to-charge ratio of the ion is, the lower the duty cycle becomes, which means that the amount of ions to be subjected to the analysis decreases and the detection sensitivity becomes lower.

To avoid this problem, a TOFMS described in Patent Literature 1 employs a method in which ions are temporarily accumulated within the collision cell 13, and the ions in the form of a mass (bunch) are discharged into the orthogonal accelerator 16 in a synchronized fashion with the ion-ejecting pulse in the orthogonal accelerator 16.

A specific description of this operation is as follows: A high voltage having the same polarity as the ions is applied to the exit lens electrode 132 of the collision cell 13 to block the ions and temporarily accumulate the ions within the collision cell 13. At a later point in time, the voltage applied to the exit lens electrode 132 is decreased, whereupon the ions compressed into a bunch-like form are discharged. After the passage of a specific length of delay time from the point in time where the voltage applied to the exit lens electrode 132 was decreased, an acceleration voltage is applied to the push-out electrode 161 and other related elements, whereby the bunch of ions discharged from the collision cell 13 are ejected into the flight space. Thus, in this TOFMS, ions which have been introduced into or generated in the collision cell 13 within a predetermined period of time can be compressed for mass spectrometry. This increases the amount of ions to be subjected to the mass spectrometry and correspondingly improves the detection sensitivity.

However, in this method, the ions which have been almost simultaneously discharged from the collision cell 13 are dispersed in the travelling direction according to their mass-to-charge ratios during their travel to the orthogonal accelerator 16. Since the OA-TOFMS and the collision cell are normally placed in different vacuum chambers separated from each other by a partition wall, the travel path from the collision cell 13 to the orthogonal accelerator 16 is comparatively long. Therefore, at the timing of the acceleration by the orthogonal accelerator 16, the ions are distributed in an elongated form along their travelling direction according to their mass-to-charge ratios, and only the ions falling within a specific mass-to-charge-ratio range will be ejected toward the flight space. Consequently, the ions falling within the specific mass-to-charge-ratio range are detected with a high level of sensitivity, while the ions outside that range cannot be observed. In the device described in Patent literature 1, the delay time mentioned earlier can be changed to adjust the range of mass-to-charge ratios which can be observed. However, when a mass spectrum covering a wide range of mass-to-charge ratios needs to be obtained, the device has problems, such as the measurement time being considerably long due to the necessity to perform the measurement multiple times while gradually changing the delay time.

In view of such a problem, various methods for achieving a high level of detection sensitivity for ions over a wide range of mass-to-charge ratios have been proposed so far.

For example, in a device described in Patent Literature 2, an area with a temporally changing electric field is provided in the previous stage of the OA-TOFMS. The temporal change of the electric field in this area is regulated to control the speed of the ions so that ions having different mass-to-charge ratios will be almost simultaneously introduced into the orthogonal accelerator.

In a device described in Patent Literature 3, an ion trap is placed in the previous stage of the OA-TOFMS. In the process of ejecting ions from the ion trap, the delay time mentioned earlier is continuously changed so that the amount of ions within a different range of mass-to-charge ratios will be increased at each ejection of the ions from the orthogonal accelerator.

In a device described in Patent Literature 4, an ion guide divided into a plurality of segments along the ion beam axis is provided in the previous stage of the OA-TOFMS. A different voltage is applied to each segment of the ion guide to make the ion guide function as an ion-accumulating unit as well as an ion-discharging unit. When ions accumulated in the ion-accumulating unit are discharged, the voltages respectively applied to the ion-accumulating unit and the ion-discharging unit are controlled so that the same amount of kinetic energy will be imparted to each of the ions having different-mass-to-charge ratios, and ions having larger mass-to-charge ratios will be discharged earlier, with the result that the ions having different mass-to-charge ratios will be almost simultaneously introduced into the orthogonal accelerator.

In a device described in Patent Literature 5, an ion guide capable of accumulating ions is provided in the previous stage of the OA-TOFMS. The accumulated ions are gradually discharged in small amounts so that the ion having the smallest mass-to-charge ratio among the accumulated ions will be discharged first, and the orthogonal accelerator is operated to eject ions for each discharging step. At every ejection of the ions, the voltage applied to each section of the device and the timing of its application are adjusted for the ions sent into the orthogonal accelerator.

Any of those various conventional devices proposed thus far requires a special ion optical system to be added, or complex control to be performed, in order to accumulate ions or control the speed of ions. Such devices have the problem of being expensive or large in size.

CITATION LIST

Patent Literature

Patent Literature 1: U.S. Pat. No. 5,689,111 A
Patent Literature 2: U.S. Pat. No. 7,087,897 B
Patent Literature 3: U.S. Pat. No. 7,208,726 B
Patent Literature 4: U.S. Pat. No. 7,456,388 B
Patent Literature 5: U.S. Pat. No. 7,714,279 B
Patent Literature 6: JP 2011-175982 A Non Patent Literature Non Patent Literature 1: M. Guilhaus and two other authors, "Orthogonal Acceleration Time-of-flight Mass Spectrometry", Mass Spectrom. Rev., Vol. 19, 2000, pp. 65-107

SUMMARY OF INVENTION

Technical Problem

The present invention has been developed to solve the previously described problem. Its objective is to provide an OA-TOFMS which can perform a high-sensitivity measurement for ions over a wide range of mass-to-charge ratios, while avoiding a complex configuration or control of the device.

Solution to Problem

The present invention developed for solving the previously described problem is an orthogonal acceleration time-of-flight mass spectrometer including an orthogonal accelerator for accelerating and ejecting ions in a direction orthogonal to the axis of incidence of ions originating from a sample and a separating-detecting section for separating and detecting the ejected ions according to their times of flight which depend on the mass-to-charge ratios of the ions, the orthogonal acceleration time-of-flight mass spectrometer including:

a) an ion-accumulating section located in the previous stage of the orthogonal accelerator, for accumulating target ions to be subjected to a measurement, the ion-accumulating section including:

a1) an ion guide including a plurality of rod electrodes arranged in such a manner as to surround a central axis, for converging ions within a space surrounded by the rod electrodes by an effect of a radio-frequency electric field, and for accelerating the ions in a direction along the central axis by a gradient of the magnitude or depth of a pseudopotential created along the central axis by the radio-frequency electric field;

a2) an exit electrode having an opening through which ions can pass, the exit electrode located at an exit end of the direction in which ions are accelerated in the ion guide; and a3) a voltage generator for applying a predetermined high radio-frequency voltage to each of the plurality of rod electrodes forming the ion guide, so as to create a radio-frequency electric field which accelerates ions in a direction along the central axis of the ion guide while converging the ions within the space surrounded by the rod electrodes, without causing a direct-current potential gradient along the central axis, and for applying a direct voltage having the same polarity as the target ions to the exit electrode to form a potential barrier and subsequently changing the direct voltage to remove the potential barrier; and b) an acceleration voltage generator for applying, to the orthogonal accelerator, a pulsed voltage for ion ejection at a point in time where a predetermined length of time elapses from a point in time where the voltage applied from the voltage generator to the exit electrode is changed to remove the potential barrier.

One preferable mode of the orthogonal acceleration time-of-flight mass spectrometer according to the present invention is a tandem mass spectrometer in which: an ion having a specific mass to charge ratio is selected by a first mass separator from among ions generated by an ion source; the selected ion is dissociated by being introduced into a collision cell in which collision-induced dissociation gas is supplied; and product ions generated by the dissociation are introduced into the orthogonal accelerator and then ejected from the orthogonal accelerator, to be separated and detected in the separating-detecting section, where the ion guide is located within the collision cell used for dissociating an ion.

In the orthogonal acceleration time-of-flight mass spectrometer according to the present invention, when a measurement for ions originating from various components contained in a sample continuously introduced into an ion source of the mass spectrometer is repeatedly performed with a predetermined period, the voltage generator repeatedly applies a predetermined direct current having the same polarity as the ions to the exit electrode with the same period and for a predetermined length of time within each period. Meanwhile, the voltage generator continuously applies a predetermined radio-frequency voltage to each of the rod electrodes forming the ion guide. In the ion guide, the various target ions to be subjected to the measurement move toward the exit end due to the gradient of the magnitude or depth of the pseudopotential, while being converged into an area near the central axis within the space surrounded by the rod electrodes due to the effect of the radio-frequency electric field. When the potential barrier formed by the direct current applied to the exit electrode is present near the same electrode, the ions which have reached an area near the exit electrode are repelled by the potential barrier.

In this situation, no direct-current potential gradient other than the potential barrier is present on the central axis of the ion guide. Therefore, the ions which have been repelled as described earlier move toward the entrance end along the central axis. Ions having smaller mass-to-charge ratios returns at higher speeds. Accordingly, ions having smaller mass-to-charge ratios more easily return to an area near the entrance end of the ion guide. As a result, ions having large mass-to-charge ratios are mainly accumulated in an area near the exit end of the ion guide, whereas ions having small mass-to-charge ratios are more broadly distributed, some of which are within an area near the exit end of the ion guide while a comparatively high proportion of those ions are within an area near the entrance end. In this situation, the voltage applied from the voltage generator to the exit electrode is changed to remove the potential barrier, whereupon the ions accumulated within the ion guide until that point in time are accelerated by the pseudopotential and sent toward the orthogonal accelerator beyond the position of the exit electrode. In this process, ions which have been located near the exit end of the ion guide, most of which have large mass-to-charge ratios, are discharged earlier. By comparison, ions which have been repelled close to the entrance end of the ion guide due to their small mass-to-charge ratios are discharged at later points in time.

Since ions having smaller mass-to-charge ratios move faster, ions which have small mass-to-charge ratios and have departed from positions close to the entrance end of the ion guide at the point in time where the voltage applied to the exit electrode is changed, i.e. at the point in time where the ion-discharging operation is initiated, will catch up with, or at least close their distance to, the ions which have large mass-to-charge ratios and have departed at earlier points in time, before the ions reach the orthogonal accelerator. When a predetermined length of delay time has elapsed since the point in time of the initiation of the ion-discharging operation, a predetermined acceleration voltage is applied from the acceleration voltage generator to the orthogonal accelerator. In the conventional case, only the ions having large mass-to-charge ratios are thereby accelerated. By comparison, in the case of the present invention, ions having small mass-to-charge ratios are also accelerated along with the ions having large mass-to-charge ratios. Thus, the effect of increasing the amount of ions by accumulating the ions in the ion-accumulating section can be obtained for a wide range of mass-to-charge ratios of the ions.

In the case where a measurement for ions originating from various components contained in a sample continuously introduced into the ion source of the mass spectrometer is repeatedly performed with a predetermined period, new ions introduced into the ion guide or ions generated by the dissociation of the introduced ions need to be accumulated within the ion guide after the previous ions have been discharged from the ion guide. Therefore, after the voltage applied to the exit electrode has been changed in order to remove the potential barrier and discharge ions, the voltage applied to the exit electrode needs to be returned to the previous state to once more form the potential barrier. That is to say, ions are discharged from the ion guide only during the discharging time in which the voltage for removing the potential barrier is applied to the exit electrode.

In order to certainly discharge ions accumulated within the ion guide, the discharging time should be long. On the other hand, if the amount of ions in each measurement period needs to be maximized, it is preferable to shorten the discharging time and elongate the time for accumulating ions. In addition, in order to avoid an unwanted mass discrepancy in the separating-detecting section, it is preferable to constantly maintain the voltage applied to each electrode during the period of time after the departure of the ions from the ion guide until they reach the orthogonal accelerator. From comprehensive consideration of these conditions, it is preferable that the point in time of the end of the discharging time, i.e. the point in time where the voltage applied from the voltage generator to the exit electrode is changed to form the potential barrier, should coincide with the point in time where the application of the acceleration voltage from the acceleration voltage generator to the orthogonal accelerator is initiated.

The pseudopotential on the central axis formed by the radio-frequency electric field in the ion guide depends on various parameters, such as the radius of the circle centered on the central axis and inscribed in the plurality of rod electrodes, the number of poles of the ion guide (e.g. number of rod electrodes), as well as the amplitude and frequency of the radio-frequency voltage applied to each rod electrode. Accordingly, it is possible to form a gradient of the magnitude or depth of the pseudopotential along the central axis by changing one of those parameters along the central axis. Based on this fact, the orthogonal acceleration time-of-flight mass spectrometer according to the present invention can be embodied in various forms.

As one specific mode of the present invention, the ion guide may include a plurality of linearly extending rod electrodes surrounding the central axis, each rod electrode arranged at an angle to the central axis in such a manner that the distance of the rod electrode from the central axis continuously increases from the entrance end toward the exit end of the ion guide.

This configuration merely requires the rod electrodes to be arranged at an angle to the central axis, instead of being arranged parallel to the central axis as in conventionally and commonly used devices. Such a configuration is simple and suppresses an increase in the cost of the device. As for the radio-frequency voltage applied to each rod electrode, only two kinds of high voltage sources which generate voltages having the same amplitude and frequency with opposite phases need to be prepared in order to simply converge ions. Therefore, the situation in which the power-system circuit become complex can also be avoided.

As another mode of the present invention, the ion guide may include a plurality of linearly extending rod electrodes surrounding the central axis, each rod electrode having a shape which partially includes an inclined portion whose distance from the central axis continuously increases from the entrance end toward the exit end of the ion guide. The inclined portion may have a linear or curved form.

As still another mode of the present invention, the ion guide may include a plurality of virtual rod electrodes surrounding the central axis, with each virtual rod electrode formed by a plurality of short rod-electrode segments separated from each other along the central axis, and the plurality of rod-electrode segments belonging to the same virtual rod electrode are arranged in such a manner that the distance of the rod-electrode segments from the central axis increases in a stepwise manner from the entrance end toward the exit end of the ion guide.

As still another mode of the present invention, the ion guide may include a plurality of linearly extending virtual rod electrodes surrounding the central axis, with each virtual rod electrode formed by a plurality of short rod-electrode segments separated from each other along the central axis, and the voltage generator applies radio-frequency voltages having different amplitudes or frequencies to the rod-electrode segments belonging to the same virtual rod electrode.

As still another mode of the present invention, the ion guide may include a plurality of linearly extending virtual rod electrodes surrounding the central axis, with each virtual rod electrode formed by a plurality of short rod-electrode segments separated from each other along the central axis, and the rod-electrode segments belonging to the same virtual rod electrode vary in cross-sectional shape. Varying the cross-sectional shape of the rod-electrode segments causes a superposition of the pseudopotential terms with different numbers of poles. This changes the shape of the pseudopotential well along the central axis, and a depth gradient of the pseudopotential can consequently be formed.

Advantageous Effects of the Invention

With the orthogonal acceleration time-of-flight mass spectrometer according to the present invention, it is possible to increase the amount of ions to be subjected to mass spectrometry and achieve high detection sensitivity for a wide range of mass-to-charge ratios of the ions, without using a complex configuration or control process. A high-sensitivity mass spectrum which covers a wide range of mass-to-charge ratios can be obtained by a single measurement, while avoiding an increase in the cost and size of the device.

BRIEF DESCRIPTION OF DRAWINGS

FIG. 11A is a front-end view of the multipole ion guide in a Q-TOF mass spectrometer according to the sixth embodiment, while

DESCRIPTION OF EMBODIMENTS

First Embodiment

A Q-TOF mass spectrometer as one embodiment (first embodiment) of the present invention is hereinafter described with reference to the attached drawings.

Figure 1:
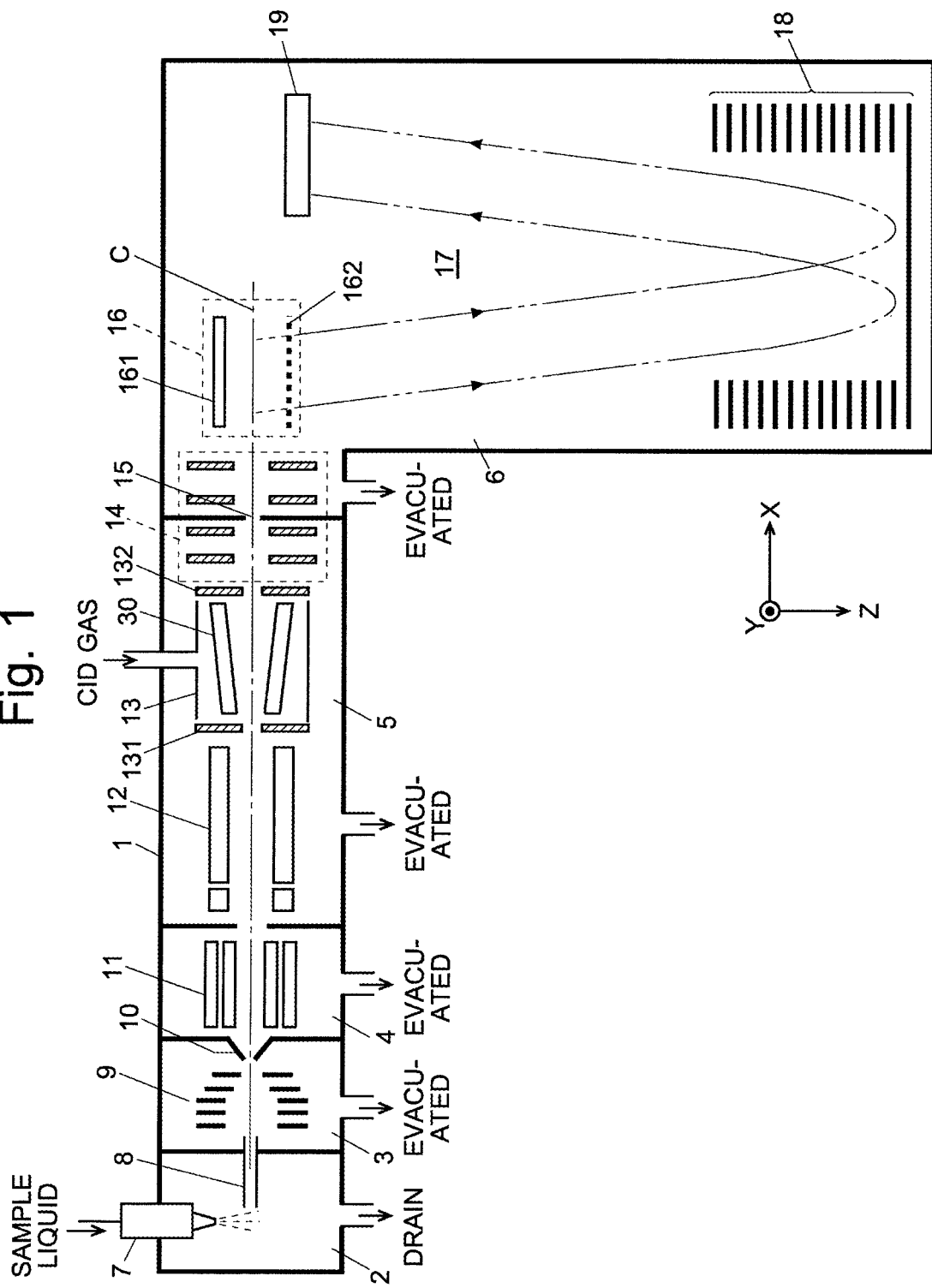
FIG. 1 is an overall configuration diagram of a Q-TOF mass spectrometer as the first embodiment of the present invention.

FIG. 1 is an overall configuration diagram of the Q-TOF mass spectrometer according to the present embodiment.

The Q-TOF mass spectrometer in the present embodiment has the configuration of a multistage pumping system, including an ionization chamber 2 maintained at substantially atmospheric pressure and a high vacuum chamber 6 with the highest degree of vacuum, with three (first through third) intermediate vacuum chambers 3, 4 and 5 located within a chamber 1 between the two aforementioned chambers 2 and 6.

The ionization chamber 2 is equipped with an ESI spray 7 for electrospray ionization (ESI). When a sample liquid containing a target component is supplied to the ESI spray 7, the sample liquid is electrostatically sprayed from the same spray 7, whereby ions originating from the target component in the sample liquid are generated. It should be noted that the ionization method is not limited to this example.

The various kinds of generated ions are sent through a heated capillary 8 into the first intermediate vacuum chamber 3, where the ions are converged by an ion guide 9 and sent through a skimmer 10 into the second intermediate vacuum chamber 4. The ions are further converged by an octapole ion guide 11 and sent into the third intermediate vacuum chamber 5. The third intermediate vacuum chamber 5 contains a quadrupole mass filter 12 and a collision cell 13, with a multipole ion guide 30 contained in the collision cell 13. The various ions derived from the sample are introduced into the quadrupole mass filter 12. Only an ion having a specific mass-to-charge ratio corresponding to the voltage applied to the quadrupole mass filter 12 is allowed to pass through the same filter 12. This ion is introduced into the collision cell 13 as the precursor ion. Due to the collision with the CID gas supplied from an external source into the collision cell 13, the precursor ion undergoes dissociation, generating various product ions.

The ion guide 30, in combination with an entrance lens electrode 131 and exit lens electrode 132, functions as a type of linear ion trap. The generated product ions are temporarily accumulated by the ion guide. Then, at a predetermined timing, the accumulated ions are discharged from the collision cell 13. Being guided by the ion transport optical system 14, those ions pass through an ion passage hole 15 and are introduced into the high vacuum chamber 6. The ion transport optical system 14 extends from the third intermediate vacuum chamber 5 to the high vacuum chamber 6, with the ion passage hole 15 sandwiched in between.

The high vacuum chamber 6 contains: an orthogonal accelerator 16; a flight space 17 with no electric field; a reflector 18 including a plurality of reflection electrodes and a back plate; and an ion detector 19. Ions introduced into the orthogonal accelerator 16 in the X-axis direction begin to fly by being accelerated in the Z-axis direction at a predetermined timing. The ions ejected from the orthogonal accelerator 16 initially fly freely through the flight space 17 and are subsequently returned by the reflecting electric field formed by the reflector 18. After flying once more freely through the flight space 17, the ions reach the ion detector 19. The time of flight required for an ion to reach the ion detector 19 after its departure from the orthogonal accelerator 16 depends on the mass-to-charge ratio of the ion. Accordingly, a data-processing unit (not shown), which receives detection signals from the ion detector 19, calculates the mass-to-charge ratio of each ion based on the time of flight of the ion and creates a mass spectrum showing the relationship between the mass-to-charge ratio and the ion intensity.

Figure 2:
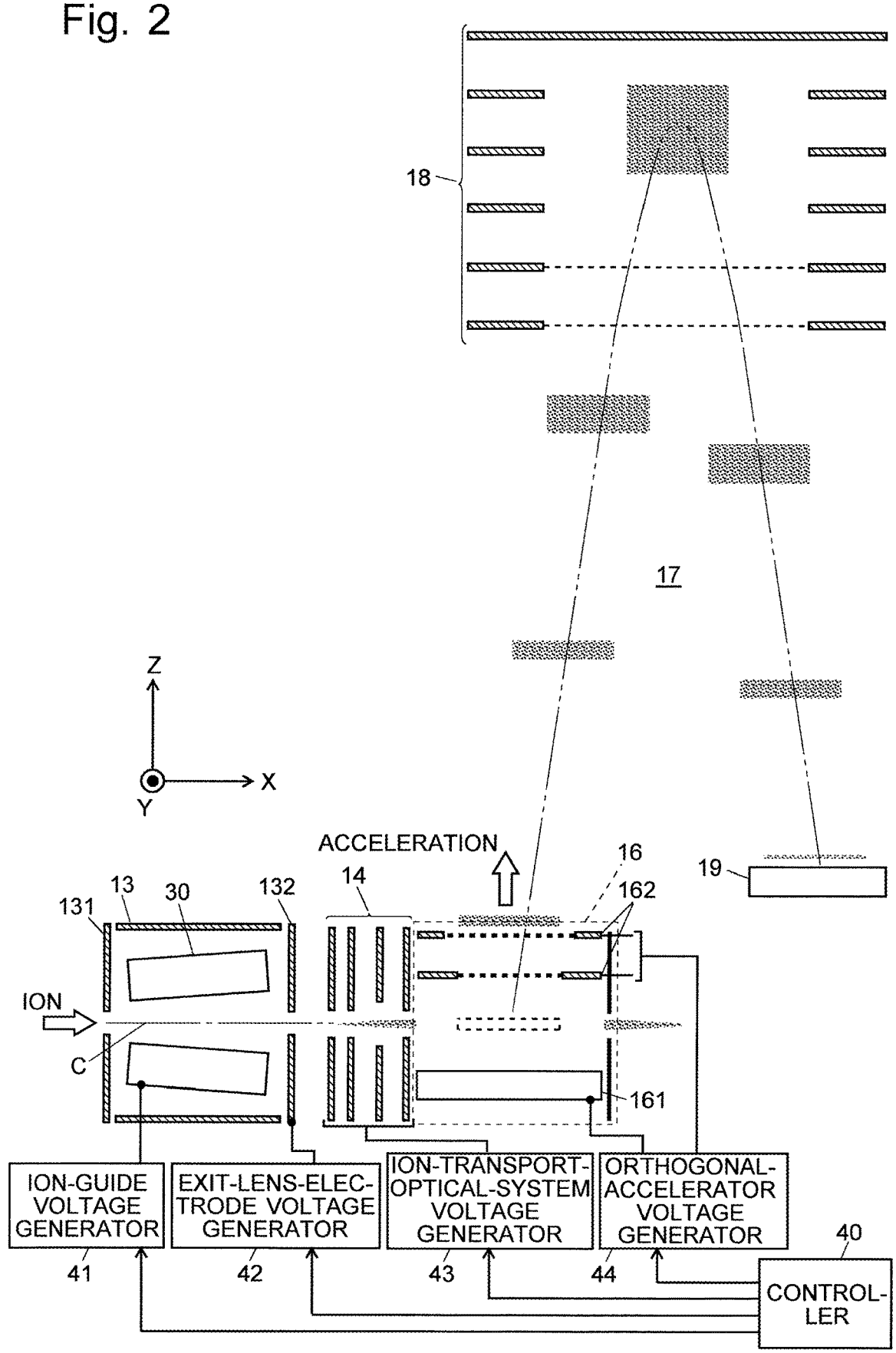
FIG. 2 is a schematic configuration diagram showing the ion optical system and control-system circuit of the collision cell and subsequent sections, which are characteristic of the Q-TOF mass spectrometer according to the first embodiment.
Figure 3B:
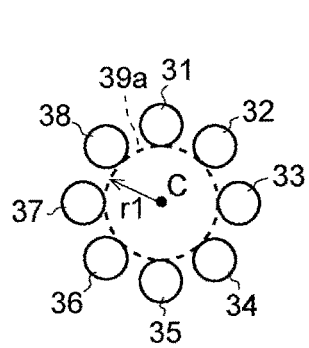
FIGS. 3A, 3B and 3C are respectively a front view, left-side view and right-side view of a multipole ion guide placed within the collision cell in the Q-TOF mass spectrometer according to the first embodiment.
Figure 3A:
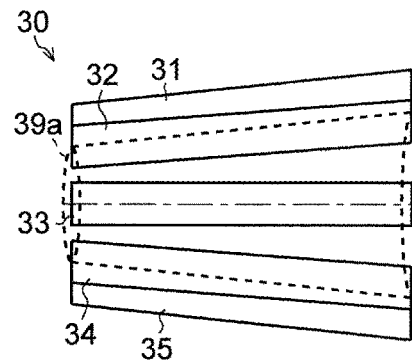
Figure 3C:
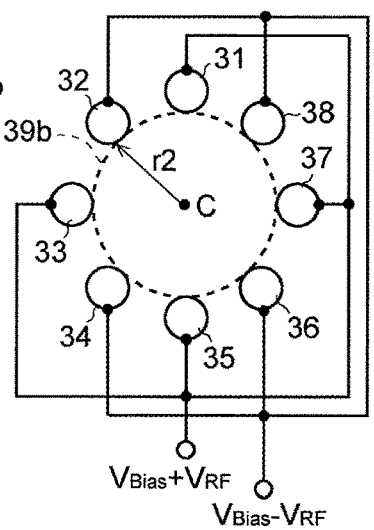

FIG. 2 is a schematic diagram showing the ion optical system and control-system circuit of the collision cell 13 and subsequent sections, which are characteristic of the Q-TOF mass spectrometer in the present embodiment. FIGS. 3A, 3B and 3C are respectively a front view, left-side view and right-side view of the ion guide 30 placed within the collision cell 13.

As shown in FIG. 2, the front-end face and rear-end face of the collision cell 13 are respectively formed by an entrance lens electrode 131 and an exit lens electrode (which corresponds to the exit electrode in the present invention) 132, each of which has a disk-like shape with a circular opening at its center. As noted earlier, the two lens electrodes 131 and 132 in combination with the ion guide 30 effectively function as a linear ion trap. The ion transport optical system 14 is formed by a number of disk-shaped plate electrodes arrayed along the central axis C, with each plate electrode having a circular opening at its center. The orthogonal accelerator 16 includes a flat-plate push-out electrode 161 extending parallel to the X-Y plane and a plurality of grid-shaped extraction electrodes 162 each of which also extends parallel to the X-Y plane.

Under the control of a controller 40, an ion-guide voltage generator (which corresponds to the voltage generator in the present invention) 41 applies a predetermined voltage to the ion guide 30, an exit-lens-electrode voltage generator (which also corresponds to the voltage generator in the present invention) 42 applies a predetermined voltage to the exit lens electrode 132, an ion-transport-optical-system voltage generator 43 applies a predetermined voltage to each plate electrode included in the ion transport optical system 14, and an orthogonal-accelerator voltage generator (which corresponds to the acceleration voltage generator in the present invention) 44 applies a predetermined voltage to each of the push-out and extraction electrodes 161 and 162. It should be noted that FIG. 2 only shows the components which are necessary for describing the characteristic operation. Needless to say, though not shown, appropriate voltages are also applied to the entrance lens electrode 131, electrodes forming the reflector 18, and other related elements.

As shown in FIG. 3, the ion guide 30 includes eight columnar rod electrodes 31-38 arranged so as to surround the central axis C, which is also the ion beam axis C. The rod electrodes 31-38 are each arranged at an angle to the central axis C in such a manner that the circle centered on the central axis C and inscribed in the eight rod electrodes 31-38 has radius r1 at the ion entrance end plane 39a and radius r2 (>r1) at the ion exit end plane 39b.

As shown in FIG. 3C, the eight rod electrodes 31-38 are divided into two groups each of which consists of four rod electrodes located at every other position in the circumferential direction. A voltage $V_{Bias}+V_{RF}$ generated by adding positive radio-frequency voltage $V_{RF}$ to direct bias voltage $V_{Bias}$ is applied from the ion-guide voltage generator 41 to the four rod electrodes 31, 33, 35 and 37 belonging to one group. Similarly, a voltage $V_{Bias}-V_{RF}$ generated by adding radio-frequency voltage $-V_{RF}$ with the opposite phase to direct bias voltage $V_{Bias}$ is applied from the ion-guide voltage generator 41 to the four rod electrodes 32, 34, 36 and 38 belonging to the other group. Due to the application of the radio-frequency voltages $\pm V_{RF}$, a radio-frequency electric field is created within the space surrounded by the eight rod electrodes 31-38. Additionally, since the rod electrodes 31-38 are obliquely arranged as described earlier, a depth gradient of the pseudopotential is formed from the entrance end toward the exit end of the ion guide 30.

As described in Patent Literature 6 or other documents, the pseudopotential Vp(R) at position R (radial distance from the central axis C) formed within the substantially cylindrical space surrounded by the ion guide 30 is expressed by the following equation (1):

$$Vp(R)=\{qn^2/(4m\Omega^2)\}\cdot(V/r)^2\cdot(R/r)^{2(n-1)} \quad (1)$$

where r is the radius of the circle inscribed in the ion guide 30, $\Omega$ is the frequency of the radio-frequency voltage, V is the amplitude of the radio-frequency voltage, n is the number of poles of the ion guide 30, m is the mass of the ion, and q is the electric charge of the ion. This equation demonstrates that the pseudopotential Vp(R) can be varied along the central axis C by changing the radius r of the circle inscribed in the ion guide 30, frequency $\Omega$ or amplitude V of the radio-frequency voltage, or number n of poles of the ion guide 30 along the central axis C. When there is a gradient (inclination) of the magnitude or depth of the pseudopotential, ions having electric charges are accelerated or decelerated along the gradient. As is evident from equation (1), the potential, or direct-current potential, on the central axis C is zero, since R=0 on the axis. Therefore, it is possible to accelerate ions within the ion guide 30 by an appropriate gradient of the magnitude or depth of the pseudopotential, without forming a direct-current potential gradient on the central axis C.

The behavior of the ions in the ion optical system including the sections from the collision cell 13 to the orthogonal accelerator 16 in the Q-TOF mass spectrometer according to the present embodiment is hereinafter described. It is hereinafter assumed that the ions are positive ions.

FIG. 4 is a timing chart of the voltages applied to the exit lens electrode 132, push-out electrode 161 and extraction electrodes 162. FIG. 5 is a model diagram for explaining the behavior of the ions.

An ion (precursor ion) having a specific mass-to-charge ratio selected by the quadrupole mass filter 12 is introduced into the collision cell 13. Upon entry into the collision cell 13, the precursor ion collides with the CID gas and undergoes dissociation. In general, an ion can be dissociated in various forms. Therefore, various product ions with different mass-to-charge ratios are generated from one kind of precursor ion by the dissociation. As described earlier, a radio-frequency electric field is created within the space surrounded by the rod electrodes 31-38 of the ion guide 30 due to the radio-frequency voltages applied to those rod electrodes 31-38. Due to this radio-frequency electric field, the ions (both the precursor ion and product ions) are converged. Although a portion of the kinetic energy originally possessed by the precursor ion is lost due to the collision with the CID gas, the ion obtains additional kinetic energy due to the depth gradient of the pseudopotential formed within the inner space of the ion guide 30. As a result, the precursor ion and product ions are accelerated toward the exit end.

Figure 4A:
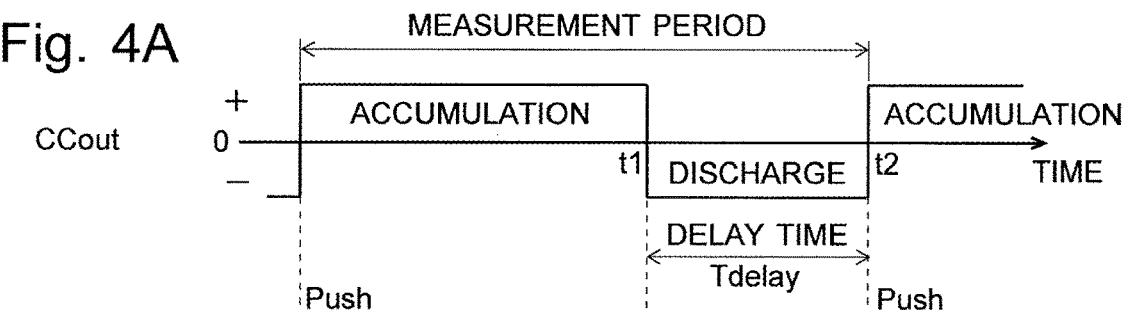
FIGS. 4A and 4B are timing charts of the voltages applied to the exit lens electrode and the orthogonal accelerator (push-out electrode and extraction electrode) in the Q-TOF mass spectrometer according to the first embodiment.
Figure 5:
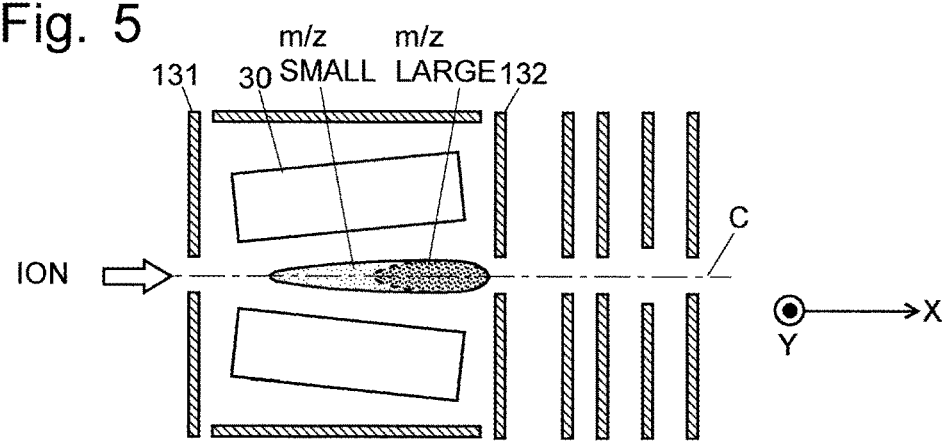
FIG. 5 is a model diagram illustrating the behavior of the ions in the Q-TOF mass spectrometer according to the first embodiment.

In the process of accumulating ions within the collision cell 13, the exit-lens-electrode voltage generator 42 applies a predetermined level of positive voltage having the same polarity as the ion to the exit lens electrode 132, as shown in FIG. 4A. A potential barrier against the ions is thereby formed at the position of the exit lens electrode 132, preventing the discharging of the ions through the exit lens electrode 132. The ions within the collision cell 13 are accelerated by the pseudopotential expressed by equation (1) and move toward the exit lens electrode 132. However, those ions are repelled by the potential barrier and return toward the exit lens electrode 132. Since no direct-current potential gradient is present on the central axis C of the ion guide 30, the repelled ions move along the central axis C toward the entrance end. The smaller the mass to charge ratio of an ion is, the higher its moving speed is. Therefore, when a certain period of time has elapsed since the point in time where a packet of ions reached an area near the exit lens electrode 132, the ions are distributed in such a manner that an ion having a smaller mass-to-charge ratio is located closer to the entrance end. FIG. 5 schematically shows this situation. Needless to say, some ions having low mass-to-charge ratios are also located near the exit end of the ion guide 30, since new ions are successively introduced into the collision cell 13, and product ions are successively generated. Nevertheless, in relative terms, a considerable amount of ions having low mass-to-charge ratios are also present on the entrance side. In summary, ions having high mass-to-charge ratios are mainly and abundantly located within a small area near the exit end, whereas ions having low mass-to-charge ratios are broadly distributed from the entrance to the exit end.

At time t1 in FIG. 4A, the voltage applied to the exit lens electrode 132 is changed to negative polarity, whereupon the potential barrier disappears. The ions located near the exit lens electrode 132, most of which have large mass-to-charge ratios, are the first to rush toward the orthogonal accelerator 16. Ions which have been returned closer to the entrance lens electrode 131 are also accelerated due to the depth gradient of the pseudopotential and slowly discharged through the exit lens electrode 132 at later points in time. As a result, at least some of the ions having low mass-to-charge ratios accumulated in the collision cell 13 are discharged from the collision cell 13 at considerably later points in time than the ions having high mass-to-charge ratios.

Figure 4B:
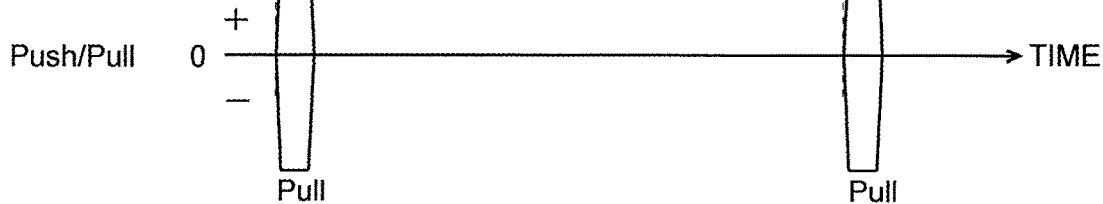

At time t2, when a specific delay time Tdelay has elapsed since the voltage applied to the exit lens electrode 132 was changed to the negative polarity (time t1), the exit-lens-electrode voltage generator 42 returns the applied voltage to the predetermined level of positive voltage having the same polarity as the ions. Synchronized with this operation, the orthogonal-accelerator voltage generator 44 applies a pulse of high positive voltage ("Push") to the push-out electrode 161 and a pulse of high negative voltage ("Pull") to the extraction electrodes 162, as shown in FIG. 4B. By this operation, the ions passing through the space between the push-out electrode 161 and the extraction electrodes 162 at the moment are accelerated in the Z-axis direction and ejected toward the flight space 17.

As described earlier, ions having low mass-to-charge ratios are delayed from ions having high mass-to-charge ratios in being discharged from the collision cell 13. However, since those ions have higher speeds, they gradually close their distance to the ions having high mass-to-charge ratios while flying through the space leading to the orthogonal accelerator 16. Accordingly, by appropriately determining the delay time Tdelay, it is possible to accelerate and eject ions passing through the space between the push-out electrode 161 and the extraction electrodes 162 at the timing when the ions having high mass-to-charge ratios are mixed with the ions having low mass-to-charge ratios which have been discharged with a delay. As a result, the ions which have been accumulated within the collision cell 13 to increase their amounts can be subjected to mass spectrometry over a wide range of mass-to-charge ratios which is not unevenly distributed on either the high mass-to-charge-ratio side or low mass-to-charge-ratio side.

As shown in FIGS. 4A and 4B, the point in time where the discharging of the ions from the collision cell 13 is discontinued to resume the accumulation of new ions is made to coincide with the point in time where the ejection of the ions in the orthogonal accelerator 16 is initiated. The reason is as follows:

Within the collision cell 13, ions are spread in the X-axis direction and it takes a certain length of time to completely discharge those accumulated ions. Therefore, in order to assuredly discharge accumulated ions from the collision cell 13, the discharging time (i.e. the period of time in which the voltage CCout in FIG. 4A has negative polarity) should be as long as possible. Furthermore, if the voltages applied to the electrodes including the exit lens electrode 132 are changed while the ions discharged from the collision cell 13 are flying toward the orthogonal accelerator 16, the change of the electric field resulting from the change in the voltages may cause a mass discrepancy in the mass spectrometry. Therefore, it is preferable to avoid changing the voltage applied to the exit lens electrode 132 while the ions discharged from the collision cell 13 are flying toward the orthogonal accelerator 16, i.e. until the ions are ejected from the orthogonal accelerator 16. In order to satisfy these two conditions, the point in time of the end of the discharging time should be set at or later than the point in time of the initiation of the application of the acceleration voltage in the orthogonal accelerator 16. On the other hand, increasing the discharging time within the specified measurement-repetition period shortens the accumulation time and correspondingly decreases the amount of ions that can be accumulated. Therefore, in order to accumulate the largest possible amount of ions, it is preferable to set the shortest possible discharging time. In order to satisfy the three aforementioned conditions as much as possible, the point in time of the end of the discharging time in the present embodiment is made to coincide with the point in time of the initiation of the application of the acceleration voltage in the orthogonal accelerator 16.

Next, an experiment for confirming the effect in the Q-TOF mass spectrometer according to the present embodiment is described. In the experiment, the frequency of ion ejection (application of the pulsed high voltages "Push" and "Pull") was set at 2 kHz. The measurement was performed, with the delay time Tdelay gradually changed, to determine to what degree the accumulation of ions increases the signal intensity of the peak at each mass-to-charge ratio, as compared to the case with no accumulation of ions. The degree of the increase in signal intensity was defined as follows: Degree of Increase of Ions=[Signal Intensity in the Case with Ion Accumulation]/[Signal Intensity in the Case without Ion Accumulation]. Accordingly, if the degree of increase of ions has the value of one, it means that the accumulation of ions has no effect. Sodium Iodide (NaI) was used as the sample for the measurement.

Figure 6:
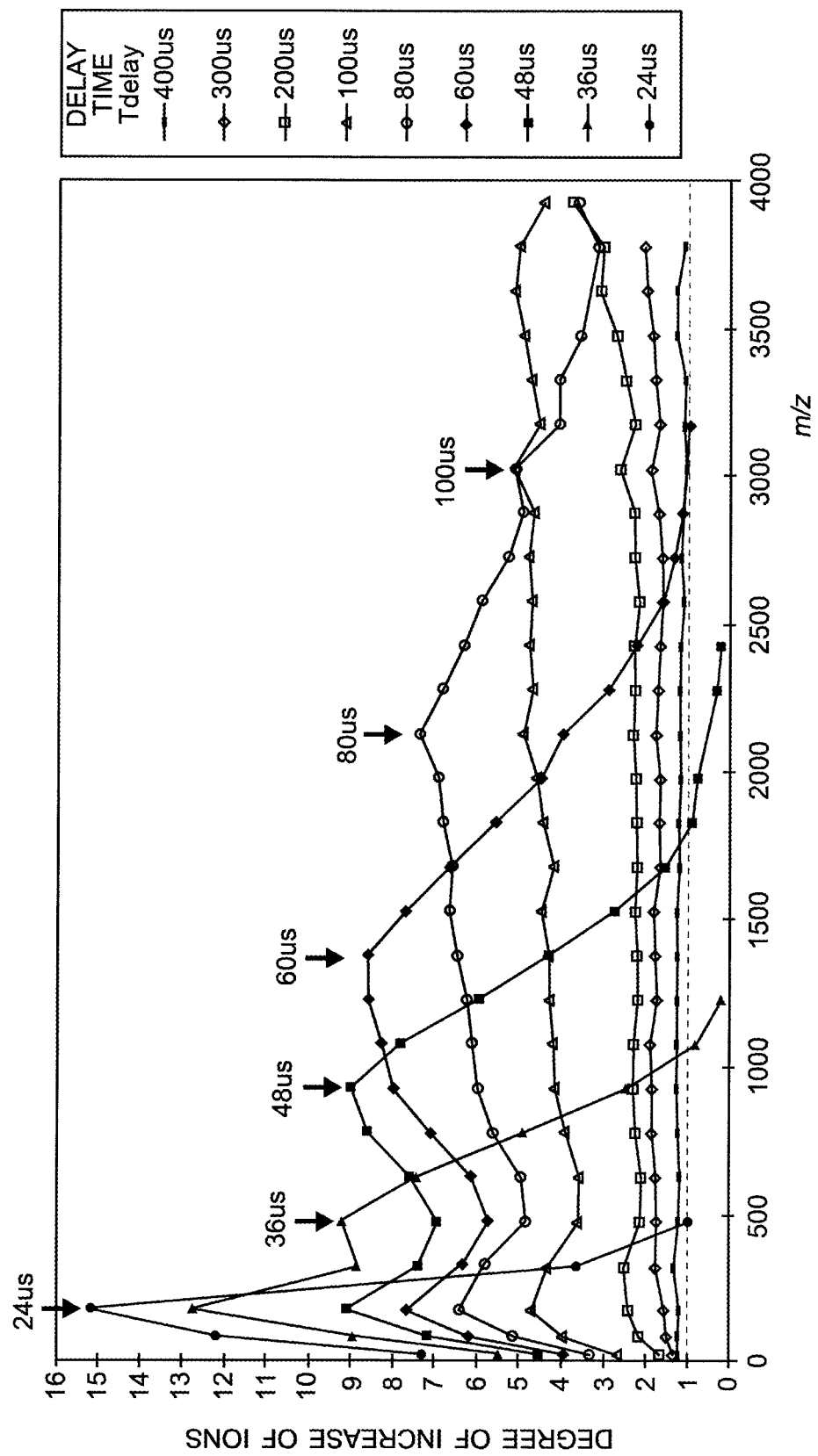
FIG. 6 is a graph showing the relationship between the mass-to-charge ratio of ions and the degree of increase of ions, with the delay time as a parameter, based on the result of a measurement.

FIG. 6 is a graph of the experimental result showing the relationship between the mass-to-charge ratio and the degree of increase of ions, with the delay time as a parameter. As indicated by the downward arrows in FIG. 6, the peak moved in the increasing direction of the mass-to-charge ratio (rightward in FIG. 6) with the increasing delay time Tdelay. This demonstrates that the degree of increase of the ions having large mass-to-charge ratios increased with the increasing delay time Tdelay. It can also be recognized that the increase in the delay time Tdelay did not cause a serious decrease in the degree of increase of the ions having small mass-to-charge ratios. That is to say, increasing the delay time Tdelay has the effect of increasing the degree of increase of the ions having large mass-to-charge ratios without causing a serious decrease in the degree of increase of the ions having small mass-to-charge ratios. This means that ions having a wide range of mass-to-charge ratios can be observed by increasing the delay time Tdelay. Such a result agrees with the previous description of the behavior of the ions.

In order to achieve the highest possible degree of increase of the ions within a mass-to-charge-ratio range that needs to be observed, the delay time Tdelay may preferably be determined according to the upper limit of the mass-to-charge-ratio range concerned. For example, referring to the result shown in FIG. 6, if it is necessary to obtain a mass spectrum within a mass-to-charge-ratio range of m/z 1000 or lower, the delay time can be set at 50 μs based on the delay time Tdelay with which the degree of increase of ions has a peak near m/z 1000. If it is necessary to obtain a mass spectrum covering a wider range of mass-to-charge ratios, for example, up to m/z 4000, the delay time Tdelay can be set around 100 μs, although the overall degree of increase becomes slightly lower. FIG. 6 also demonstrates that a further increase in the delay time Tdelay noticeably lowers the effect of the accumulation of ions, and the degree of increase of ions converges to the value of one. Thus, the effect of accumulating ions within the collision cell 13 can be sufficiently produced by determining the delay time according to the mass-to-charge-ratio range to be observed, and particularly, according to its upper limit.

As described to this point, the Q-TOF mass spectrometer according to the present embodiment can sufficiently exhibit the effect of the accumulation of ions within the collision cell 13 for a wide range of mass-to-charge ratios of the ions and thereby enable a high-sensitivity observation of each ion.

As noted earlier, the gradient of the pseudopotential along the central axis C within the collision cell 13 can also be formed by changing the radius of the circle inscribed in the ion guide 30, frequency or amplitude of the radio-frequency voltage applied to the rod electrodes 31-38, number of poles of the ion guide 30, or other related parameters along the central axis C. Accordingly, the configuration of the ion guide 30 in the first embodiment can be changed to various forms, as will be hereinafter described. FIGS. 7-11 each show the configuration of the ion guide in a Q-TOF mass spectrometer according to another embodiment of the present invention.

Second Embodiment

Figure 7:
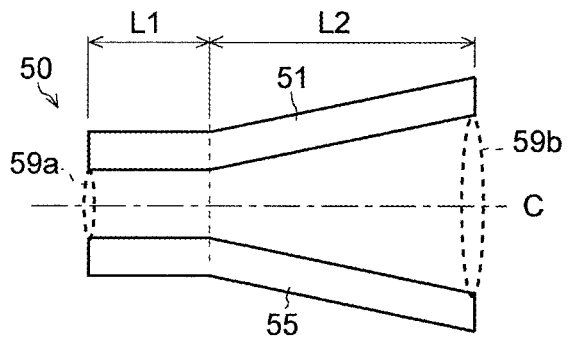
FIG. 7 is a front-end view of the multipole ion guide in a Q-TOF mass spectrometer according to the second embodiment.

FIG. 7 is a front-end view of an ion guide 50 to be placed within the collision cell in a Q-TOF mass spectrometer according to the second embodiment. In this ion guide 50, each of the rod electrodes (only two of them denoted by numerals 51 and 55 are shown in FIG. 7, although there are actually eight rod electrodes, as in the first embodiment) is bent at a halfway point. The radius of the circular opening 59b at the exit end plane is thereby made to be larger than that of the circular opening 59a at the entrance end plane. No gradient of the pseudopotential is present within section L1 where the rod electrodes are parallel to the central axis C, whereas the pseudopotential has a gradient similar to the first embodiment within section L2 where the rod electrodes are at an angle to the central axis C. Accordingly, the Q-TOF mass spectrometer according to the second embodiment including this ion guide 50 produces similar effects to those described in the first embodiment.

Third Embodiment

Figure 8:
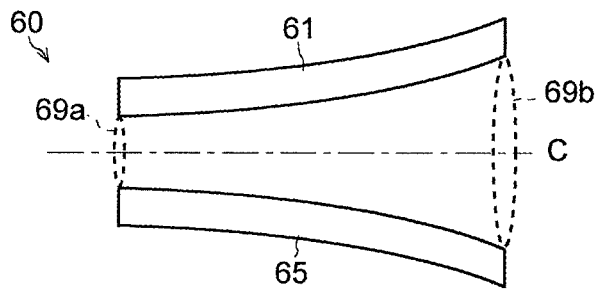
FIG. 8 is a front-end view of the multipole ion guide in a Q-TOF mass spectrometer according to the third embodiment.

FIG. 8 is a front-end view of an ion guide 60 to be placed within the collision cell in a Q-TOF mass spectrometer according to the third embodiment. In this ion guide 60, each of the rod electrodes (only two of them denoted by numerals 61 and 65 are shown in FIG. 8, although there are actually eight rod electrodes, as in the first embodiment) has a curved shape. The radius of the circular opening 69b at the exit end plane is thereby made to be larger than that of the circular opening 69a at the entrance end plane, and furthermore, it is guaranteed that the radius gradually increases from the entrance end toward the exit end. Accordingly, the Q-TOF mass spectrometer according to the third embodiment including this ion guide 60 produces similar effects to those described in the first embodiment.

Fourth Embodiment

Figure 9A:
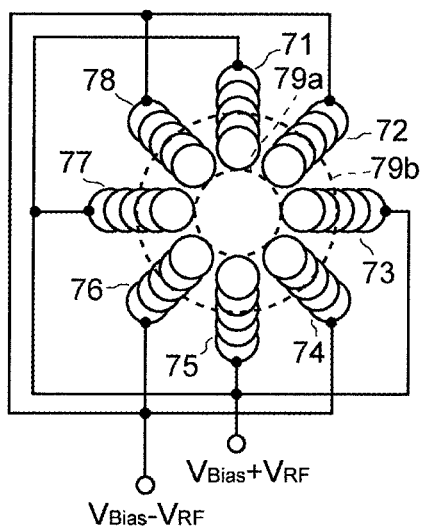
FIGS. 9A and 9B are respectively a left-side view and a front-end view of the multipole ion guide in a Q-TOF mass spectrometer according to the fourth embodiment.
Figure 9B:
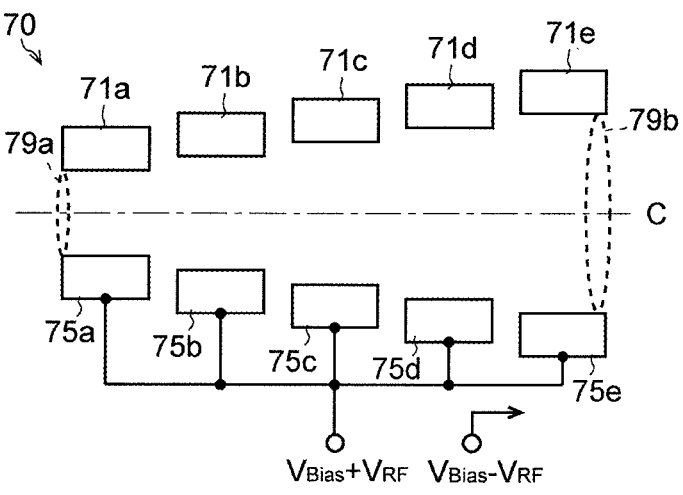

FIGS. 9A and 9B are respectively a left-side view and a front-end view of an ion guide 70 to be placed within the collision cell in a Q-TOF mass spectrometer according to the fourth embodiment. In this ion guide 70, each rod electrode is not a single continuously-extending electrode, but a virtual rod electrode (e.g. numeral 71) consisting of a plurality of (in the present example, five) rod-electrode segments separated from each other along the central axis C (e.g. numerals 71a-71e). There are eight virtual rod electrodes 71-78 arranged in such a manner as to surround the central axis C. In each of the virtual rod electrodes 71-78, the rod-electrode segments (e.g. 71a-71e) are arranged in such a manner that their distance from the central axis C increases in a stepwise manner from the entrance end toward the exit end. This ion guide 70 can be considered to be an ion guide formed by eight rod electrodes arranged in such a manner as to surround the central axis C, as in the first embodiment. Accordingly, the Q-TOF mass spectrometer according to the fourth embodiment including this ion guide 70 produces similar effects to those described in the first embodiment.

Fifth Embodiment

Figure 10:
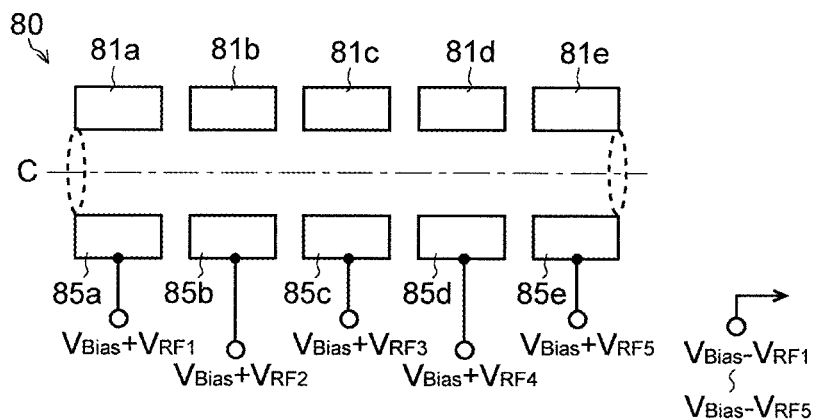
FIG. 10 is a front-end view of the multipole ion guide in a Q-TOF mass spectrometer according to the fifth embodiment.

FIG. 10 is a front-end view of an ion guide 80 to be placed within the collision cell in a Q-TOF mass spectrometer according to the fifth embodiment. Similar to the fourth embodiment, this ion guide 80 includes virtual rod electrodes (only two of them denoted by numerals 81 and 85 are shown in FIG. 10, although there are actually eight rod electrodes, as in the first embodiment) arranged in such a manner as to surround the central axis C, with each virtual rod electrode consisting of a plurality of rod-electrode segments. It should be noted that the rod-electrode segments belonging to the same virtual rod electrode are located at the same distance from the central axis C. In other words, the circular opening of the virtual rod electrode has the same radius at any position on the central axis C. Instead of changing the radius of the circular opening, the device is configured to apply different radio-frequency voltages $V_{RF1}$-$V_{RF5}$ to the rod-electrode segments belonging to the same virtual rod electrodes (e.g. numerals 85a-85e). The gradient of the magnitude or depth of the pseudopotential along the central axis C is formed by changing the frequency or amplitude of those radio-frequency voltages $V_{RF1}$-$V_{RF5}$, or both of them, in a stepwise manner. Accordingly, the Q-TOF mass spectrometer according to the fifth embodiment including this ion guide 80 produces similar effects to those described in the first embodiment.

Sixth Embodiment

Figure 11A:
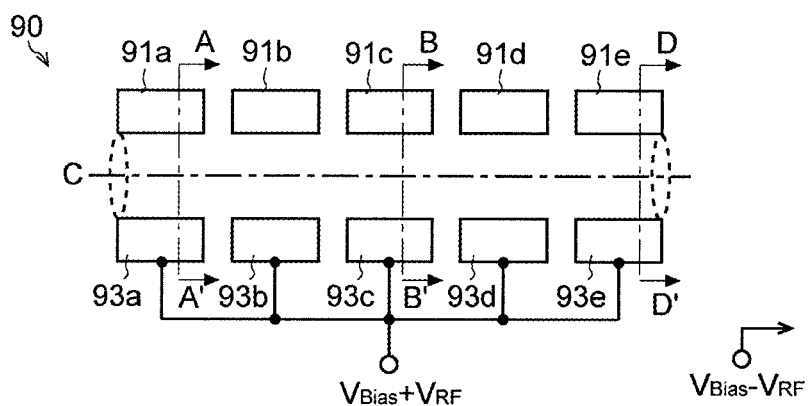
Figure 11B:
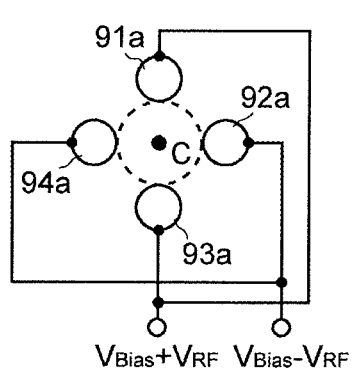
FIGS. 11B, 11C and 11D are end views of the same ion guide at the cross sections indicated by the respective arrows.
Figure 11C:
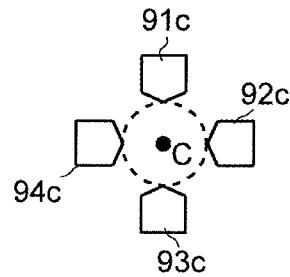
Figure 11D:
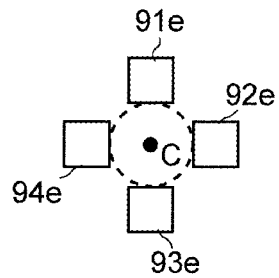
Figure 12:
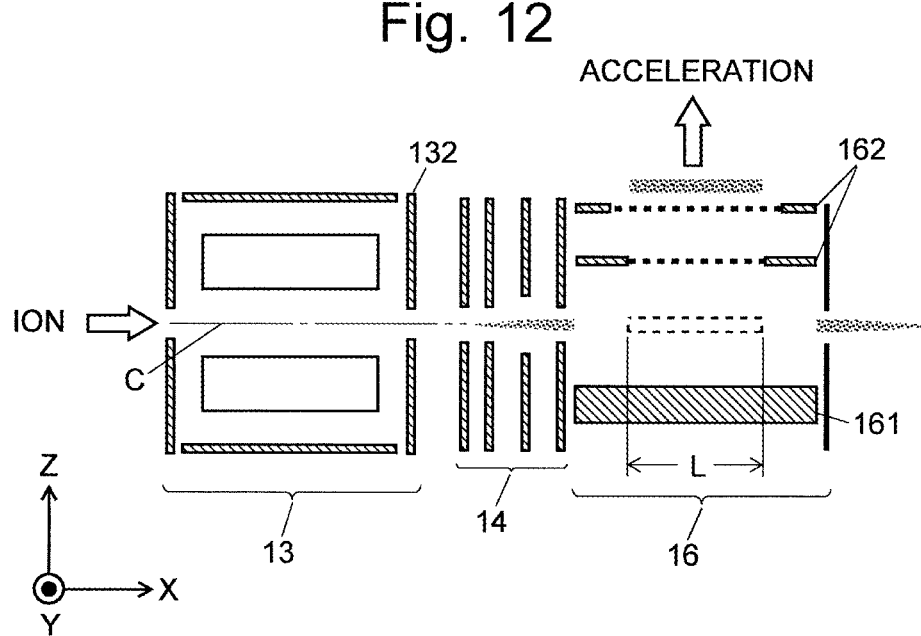
FIG. 12 is a schematic diagram of an ion optical system including the sections from the collision cell to the orthogonal accelerator in a conventional Q-TOF mass spectrometer.

FIG. 11A is a front-end view of an ion guide 90 to be placed within the collision cell in a Q-TOF mass spectrometer according to the sixth embodiment, while FIGS. 11B, 11C and 11D are end views of the same ion guide at the cross sections indicated by the respective arrows. This ion guide 90 includes four virtual rod electrodes 91-94 arranged in such a manner as to surround the central axis C, with each rod electrode consisting of a plurality of rod-electrode segments, as in the fourth or fifth embodiment. It should be noted that the same radio-frequency voltage $\pm V_{RF}$ is applied to the rod-electrode segments belonging to the same virtual rod electrode. Instead of applying different radio-frequency voltages, the device uses the rod-electrode segments which vary in cross-sectional shape. Specifically, for example, the virtual rod electrode 91 includes rod-electrode segments 91a and 91b having a circular cross section as shown in FIG. 11B, rod-electrode segments 91c and 91d having a pentagonal cross section as shown in FIG. 11C, and rod-electrode segment 91e having a square cross-section as shown in FIG. 11D.

When rod-electrode segments which vary in cross-sectional shape are used in the previously described manner, or more specifically, when rod-electrode segments having a non-circular cross-sectional shape are used, pseudopotential terms with different number of poles n will be superposed on each other in equation (1), which changes the form of the pseudopotential. This allows for the formation of an effective gradient of the magnitude or depth of the pseudopotential. Accordingly, the Q-TOF mass spectrometer according to the sixth embodiment including this ion guide 90 produces similar effects to those described in the first embodiment.

It should be noted that the previous embodiments are mere examples of the present invention, and any change, modification or addition appropriately made within the spirit of the present invention will evidently fall within the scope of claims of the present application.

REFERENCE SIGNS LIST

1 . . . Chamber
2 . . . Ionization Chamber
3 . . . First Intermediate Vacuum Chamber
4 . . . Second Intermediate Vacuum Chamber
5 . . . Third Intermediate Vacuum Chamber
6 . . . High Vacuum Chamber
7 . . . ESI Spray
8 . . . Heated Capillary
10 . . . Skimmer
9, 11 . . . Ion Guide
12 . . . Quadrupole Mass Filter
13 . . . Collision Cell
131 . . . Entrance Lens Electrode
132 . . . Exit Lens Electrode
14 . . . Ion Transport Optical System
15 . . . Ion Passage Hole
16 . . . Orthogonal Accelerator
161 . . . Push-Out Electrode
162 . . . Extraction Electrode
17 . . . Flight Space
18 . . . Reflector
19 . . . Ion Detector
20 . . . Radio-Frequency Ion Guide
30, 50, 60, 70, 80, 90 . . . Multipole Ion Guide
31-38 . . . Rod Electrode
39a . . . Ion Entrance End Plane
39b . . . Ion Exit End Plane
40 . . . Controller
41 . . . Ion-Guide Voltage Generator
42 . . . Exit-Lens-Electrode Voltage Generator
43 . . . Ion-Transport-Optical-System Voltage Generator
44 . . . Orthogonal-Accelerator Voltage Generator
C . . . Central Axis (Ion Beam Axis)

The invention claimed is:

1. An orthogonal acceleration time-of-flight mass spectrometer including an orthogonal accelerator configured to accelerate and eject ions in a direction orthogonal to an axis of incidence of ions originating from a sample and a separating-detecting section configured to separate and detect the ejected ions according to their times of flight which depend on mass-to-charge ratios of the ions, the orthogonal acceleration time-of-flight mass spectrometer comprising:

a) an ion-accumulating section located in a previous stage of the orthogonal accelerator, configured to accumulate target ions to be subjected to a measurement, the ion-accumulating section including:
  a1) an ion guide including a plurality of rod electrodes arranged in such a manner as to surround a central axis, configured to converge ions within a space surrounded by the rod electrodes by an effect of a radio-frequency electric field, and configured to accelerate the ions in a direction along the central axis by a gradient of the magnitude or depth of a pseudopotential created along the central axis by the radio-frequency electric field;
  a2) an exit electrode having an opening through which ions are capable of passing, the exit electrode located at an exit end of the direction in which ions are accelerated in the ion guide; and
  a3) a voltage generator configured to apply a predetermined high radio-frequency voltage to each of the plurality of rod electrodes forming the ion guide, and apply a direct voltage having a same polarity as the target ions to the exit electrode to form a potential barrier and subsequently changing the direct voltage to remove the potential barrier, so as to create, without causing a direct-current potential gradient along the central axis, a radio-frequency electric field which accelerates the ions in the direction along the central axis of the ion guide while converging the ions within the space surrounded by the rod electrodes; and
b) an acceleration voltage generator configured to apply, to the orthogonal accelerator, a pulsed voltage for ion ejection at a point in time where a predetermined length of time elapses from a point in time where the voltage applied from the voltage generator to the exit electrode is changed to remove the potential barrier.

2. The orthogonal acceleration time-of-flight mass spectrometer according to claim 1, wherein:
the ion guide is located within a collision cell to which collision-induced dissociation gas is supplied to dissociate an ion.

3. The orthogonal acceleration time-of-flight mass spectrometer according to claim 1, wherein:
the orthogonal acceleration time-of-flight mass spectrometer is configured to repeatedly perform, with a predetermined period, a measurement for ions originating from various components contained in a sample continuously introduced into an ion source; and
a timing of control of voltage application is set so that a point in time where the voltage applied from the voltage generator to the exit electrode is changed to form the potential barrier coincides with a point in time where application of the accelerating voltage from the acceleration voltage generator to the orthogonal accelerator is initiated.

4. The orthogonal acceleration time-of-flight mass spectrometer according to claim 1, wherein:
the ion guide includes a plurality of linearly extending rod electrodes surrounding the central axis, each rod electrode arranged at an angle to the central axis in such a manner that a distance of the rod electrode from the central axis continuously increases from an entrance end toward an exit end of the ion guide.

5. The orthogonal acceleration time-of-flight mass spectrometer according to claim 1, wherein:
the ion guide includes a plurality of linearly extending rod electrodes surrounding the central axis, each rod electrode having a shape which partially includes an inclined portion whose distance from the central axis continuously increases from an entrance end toward an exit end of the ion guide.

6. The orthogonal acceleration time-of-flight mass spectrometer according to claim 1, wherein:
the ion guide includes a plurality of virtual rod electrodes surrounding the central axis, with each virtual rod electrode formed by a plurality of short rod-electrode segments separated from each other along the central axis, and the plurality of rod-electrode segments belonging to a same virtual rod electrode are arranged in such a manner that a distance of the rod-electrode segments from the central axis increases in a stepwise manner from an entrance end toward an exit end of the ion guide.

7. The orthogonal acceleration time-of-flight mass spectrometer according to claim 1, wherein:
the ion guide includes a plurality of linearly extending virtual rod electrodes surrounding the central axis, with each virtual rod electrode formed by a plurality of short rod-electrode segments separated from each other along the central axis, and the voltage generator is configured to apply radio-frequency voltages having different amplitudes or frequencies to the rod-electrode segments belonging to a same virtual rod electrode.

8. The orthogonal acceleration time-of-flight mass spectrometer according to claim 1, wherein:
the ion guide includes a plurality of linearly extending virtual rod electrodes surrounding the central axis, with each virtual rod electrode formed by a plurality of short rod-electrode segments separated from each other along the central axis, and the rod-electrode segments belonging to the same virtual rod electrode vary in cross-sectional shape.

* * * * *